US011713460B2

(12) United States Patent
Kieft et al.

(10) Patent No.: US 11,713,460 B2
(45) **Date of Patent: *Aug. 1, 2023**

(54) PROTECTING RNAS FROM DEGRADATION USING ENGINEERED VIRAL RNAS

(71) Applicant: The Regents of the University of Colorado, Denver, CO (US)

(72) Inventors: Jeffrey S. Kieft, Denver, CO (US); Erich G. Chapman, Denver, CO (US); David A. Costantino, Denver, CO (US); Jay R. Hesselberth, Denver, CO (US); Andrea MacFadden, Denver, CO (US); Benjamin Akiyama, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/173,354

(22) Filed: Feb. 11, 2021

(65) Prior Publication Data

US 2021/0332357 A1 Oct. 28, 2021

Related U.S. Application Data

(63) Continuation of application No. 16/064,174, filed as application No. PCT/US2016/066723 on Dec. 14, 2016, now Pat. No. 10,920,224.

(60) Provisional application No. 62/270,986, filed on Dec. 22, 2015.

(51) Int. Cl.
*C07H 21/04* (2006.01)
*C12N 15/113* (2010.01)

(52) U.S. Cl.
CPC ........ *C12N 15/113* (2013.01); *C12N 2310/18* (2013.01); *C12N 2310/531* (2013.01)

(58) Field of Classification Search
None
See application file for complete search history.

(56) References Cited

PUBLICATIONS

Chapman et al., "RNA structure that resist degradation by Xrn1 produce a pathogenic Dengue virus RNA," eLIFE (2014), 25 pages.
Communication Pursuant to Rule 164(1) EPC, EP Application No. 16879894.0, dated Apr. 24, 2019.
European Search Report, EP Application No. 16879894.0, dated Jan. 20, 2020, 11 pages.
Moon, Stephanie L., "Inhibition of the Host 5'-3' RNA Decay Pathway is a Novel Mechanism by Which Flaviviruses Influence Cellular Gene Expression," Ph.D. Thesis (2014), pp. 76, 128, 133, and 220.
Notffication Concerning Transmittal of International Preliminary Report on Patentability, PCT/US2016/066723, dated Jul. 5, 2018, 7 pages.
Notification of Transmittal of the International Search Report and the Written Opinion of the International Searching Authority or the Declaration, PCT/US16/66723, dated Jun. 12, 2017.
Olbris, Mark, "Self Cleavage by the Hepatitis & Virus Ribozyme," (2005), 5 pages.
Ruehle et al., "A dynamic RNA loop in an IRES affects multiple steps of elongation factor-mediated translation initiation," eLIFE, (2015), 24 pages.
Silva et al., "An RNA Pseudoknot is Required for Production of Yellow Fever Virus Subgenomic RNA by the Host Nuclease XRN1," Journal of Virology, Nov. 2010, vol. 84, No. 21, pp. 11395-11406.
Yang et al. "Studies of the 5' Exonuclease and Endonuclease Activities of CPSF-73 in Histone Pre-mRNA Processing," Mol Cell Biol. (2009) 29 (1), pp. 31-42.

*Primary Examiner* — Kimberly Chong
(74) *Attorney, Agent, or Firm* — Stanek Lemon Crouse & Meeks, PA

(57) ABSTRACT

This invention is in the field of molecular biology, gene expression, functional genomics, and bioinformatics and relates to novel RNA and related structures and methods of use thereof that enables modulation of gene expression and preservation of particular transcriptome targets. The invention contemplates various applications of RNA sequences derived from the genomic RNA of flaviviruses (FVs) and the application of such features in combination with heterologous sequences.

20 Claims, 16 Drawing Sheets

Specification includes a Sequence Listing.

RNA

PS RNA

BO RNA

4'-thio RNA

LNA

2'-O-MOE RNA

2'-O-methyl RNA

2'-Fluoro RNA

FANA

Ribo-difluorotolyl

Morpholino

PNA

PROTECTING RNAS FROM DEGRADATION USING ENGINEERED VIRAL RNAS

CROSS-REFERENCE TO RELATED APPLICATIONS

The present application is a continuation of U.S. patent application Ser. No. 16/064,174, now U.S. Pat. No. 10,920,224, filed Jun. 20, 2018, which is a U.S. national phase application under 35 U.S.C. § 371 of PCT International Application No. PCT/US2016/066723, filed Dec. 4, 2016, which claims the benefit of U.S. Provisional Patent Application No. 62/270,986, filed Dec. 22, 2015, the disclosures of each of which is incorporated herein by reference.

STATEMENT OF GOVERNMENTAL SUPPORT

This invention was made with government support under grant number GM108257 awarded by National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 1510077-00040_ST25.txt, 1,045 bytes in size, generated on Feb. 1, 2023, and filed electronically, is provided in lieu of a paper copy. This Sequence Listing is hereby incorporated herein by reference into the specification for its disclosures.

FIELD OF THE INVENTION

This invention is in the field of molecular biology, gene expression, functional genomics, and bioinformatics and relates to novel RNA and related structures and methods of use thereof that enables modulation of gene expression and preservation of particular transcriptome targets. The invention contemplates various applications of RNA sequences derived from the genomic RNA of flaviviruses (FVs) and the application of such features in combination with heterologous sequences.

BACKGROUND OF THE INVENTION

The term transcriptome can be applied to the total set of transcripts in a given organism, or to the specific subset of transcripts present in a particular cell type. Unlike the genome, which is roughly fixed for a given cell line (excluding mutations), the transcriptome can vary with external environmental conditions and internal processes. RNA transcripts are particularly susceptible to degradation by exonucleases, and this process is used by cells to control the abundance of specific transcripts in the cell. Because the transcriptome includes all mRNA transcripts in the cell, the transcriptome reflects the genes that are being actively expressed at any given time and the mRNA that is present in the cell that has not been degraded by the cellular RNA turnover processes. In certain situations, there may be a desire to prolong the existence of particular RNA transcripts and to specifically target said transcript. What are needed are structures and methods for specifically altering the transcriptome. Such a method may be useful in applications in molecular biology, medicine, and agriculture for example where manipulation of the transcriptome could play a role.

SUMMARY OF THE INVENTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

This invention is in the field of molecular biology, gene expression, functional genomics, and bioinformatics and relates to novel RNA and related structures and methods of use thereof that enables modulation of gene expression and preservation of particular transcriptome targets. The invention contemplates various applications of RNA sequences derived from the genomic RNA of flaviviruses (FVs) and the application of such features in combination with heterologous sequences.

In one embodiment, the invention contemplates various applications of RNA sequences derived from flaviviruses (FVs). These RNA sequences have been found to be resistant to cellular enzyme Xrn1, the dominant cytoplasmic 5'→3' exonuclease. These discrete Xrn1-halting sequences are referred to as "Xrn1-resistant RNAs" (xrRNAs). The xrRNAs have been found to have distinct structural elements and further have certain conserved sequences to retain these resistant structural elements and enable the resultant resistant behavior.

In one embodiment, the invention contemplates that such sequences of RNA could be useful in a number of applications including, but not limited to: A) introduction of an xrRNA sequence "in cis" upstream of desired heterologous mRNA sequences to improve the half-life of the heterologous mRNA sequences by protecting the RNA from exonuclease degradation; and B) provide Xrn1 nuclease resistance by the "in trans" association of an RNA that provides Xrn1-halting ability to an RNA that does not have this ability, thus protecting a "target" RNA from degradation by hybridization of a "protecting" RNA. In this approach, structures similar to xrRNAs could be generated by the hybrid association of two heterologous RNAs rather than placing an xrRNA sequence on at least one heterologous RNA sequence.

In one embodiment, the invention contemplates that the "in trans" configuration could be used: (1) to alter specific endogenous RNA degradation rates within cells as a "transcriptome editing" tool and (2) coupling such RNA combinations with a way to turn protected (but uncapped or decapped) mRNAs into viable translation templates as a "translatome editing" tool. It is believed by adjustment of the RNA sequence, that the "protecting RNA" could be "tuned" to achieve various protection levels and translation levels of endogenous RNAs.

In one embodiment, the invention contemplates a synthetic ribonucleic acid (RNA) sequence comprising an exonuclease resistant RNA sequence embedded upstream (5') of a heterologous RNA sequence, wherein said exonuclease resistant RNA sequence comprises an interwoven pseudoknot structure. In one embodiment, said interwoven pseudoknot structure comprises a conserved three-way junction. In one embodiment, said synthetic RNA sequence further comprises an internal ribosome entry site sequence between said exonuclease resistant RNA sequence and said heterologous RNA sequence. In one embodiment, said synthetic RNA sequence further comprises at least one chemical modification at either the 5'-end or 3'-end. In one embodiment, said synthetic RNA sequence further comprises at least one chemical modification at either the 5'-end or 3'-end.

In one embodiment, the invention contemplates a synthetic ribonucleic acid (RNA) duplex comprising a first exonuclease resistant RNA sequence hybridized to a second heterologous RNA sequence, wherein a region of said first exonuclease resistant RNA sequence and a region of said second heterologous RNA sequence comprise an interwoven pseudoknot structure that forms an exonuclease-resistant structure. In one embodiment, said interwoven pseudoknot structure comprises a conserved three-way junction. In one embodiment, said second heterologous RNA sequence comprises a naturally occurring RNA sequence. In one embodiment, said first exonuclease resistant RNA sequence further comprises a heterologous RNA sequence ligated or attached to the 3' end of said exonuclease resistant RNA sequence. In one embodiment, said heterologous RNA sequence comprises small molecule sensing riboswitch. In one embodiment, said first sequence further comprises a translation initiation element. In one embodiment, said riboswitch disrupts the interwoven pseudoknot structure in the presence of said small molecule. In one embodiment, said heterologous RNA sequence comprises an open reading frame. In one embodiment, said heterologous RNA sequence comprises a protein binding sequence. In one embodiment, said heterologous RNA sequence comprises a Spinach sequence or other similar RNA sequence capable of fluorescence-based visualization. In one embodiment, said synthetic RNA duplex comprises a chemical modification of either the 5' end or 3' end. In one embodiment, said synthetic RNA duplex comprises at least one chemically modified nucleotide.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "transcriptome" is used throughout the specification to describe the set of all RNA molecules, including mRNA, rRNA, tRNA, and other non-coding RNA transcribed in one cell or a population of cells. It differs from the exome in that it includes only those RNA molecules found in a specified cell population, and usually includes the amount or concentration of each RNA molecule in addition to the molecular identities.

As used herein, the term "exonuclease" is used throughout the specification to describe an enzyme that degrades nucleic acid in a directional manner; that is by interacting with one end of a nucleic acid molecule and degrading it in a stepwise (one nucleotide at a time) manner by progressing to the other end of the molecule (either 5'→3' or 3'→5').

As used herein, the term "endonuclease" is used throughout the specification to describe an enzyme that cleaves a nucleic acid internally; that is, by separating nucleotides within the sequence and not at the ends of the nucleic acid chain.

As used herein, the term "internal ribosome entry site" or "IRES" is used throughout the specification to describe a nucleotide sequence that allows for translation initiation in the middle of a messenger RNA (mRNA) sequence. Thus, IRESs drive cap- and end-independent translation of an mRNA.

As used herein, the term "pseudoknot" is used throughout the specification to describe an RNA base-pairing structural scheme in which an RNA loop is base-paired to a region located outside (upstream or downstream) of the stem that flanks or creates the loop.

The terms "coupled", "connected", "attached", "linked", or "conjugated" are used interchangeably herein and encompass direct as well as indirect connection, attachment, linkage, or conjugation unless the context clearly dictates otherwise. The attachment of a ligand to a bead may be covalent or non-covalent. Attachment may be reversible or irreversible. Such attachment includes, but is not limited to, covalent bonding, ionic bonding, Van der Waals forces or friction, and the like.

The term "a means for detecting" as used herein, refers to any method and/or device that is capable of individually sensing each subset of a solid particle population, even if the subset comprises a single solid particle. For example, the means may be a flow cytometer that detects the solid particles using laser scanning.

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from five nucleotide residues to the entire nucleotide sequence minus one nucleic acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast, "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

As used herein, the term "antisense" is used in reference to RNA sequences, which are complementary to a specific RNA sequence (e.g., mRNA). Antisense RNA may be produced by any method, including synthesis by splicing the gene(s) of interest in a reverse orientation to a viral promoter, which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the terms "siRNA" refers to either small interfering RNA, short interfering RNA, or silencing RNA. Generally, siRNA comprises a class of double-stranded RNA molecules, approximately 20-25 nucleotides in length. Most notably, siRNA is involved in RNA interference (RNAi) pathways and/or RNAi-related pathways. wherein the compounds interfere with gene expression.

As used herein, the term "shRNA" refers to any small hairpin RNA or short hairpin RNA. Although it is not necessary to understand the mechanism of an invention, it is believed that any sequence of RNA that makes a tight hairpin turn can be used to silence gene expression via RNA interference. Typically, shRNA uses a vector stably introduced into a cell genome and is constitutively expressed by a compatible promoter. The shRNA hairpin structure may also cleaved into siRNA, which may then become bound to the RNA-induced silencing complex (RISC). This complex binds to and cleaves mRNAs which match the siRNA that is bound to it.

As used herein, the term "microRNA", "miRNA", or "RNA" refers to any single-stranded RNA molecules of approximately 21-23 nucleotides in length, which regulate gene expression. miRNAs may be encoded by genes from whose DNA they are transcribed but miRNAs are not translated into protein (i.e. they are non-coding RNAs). Each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

The term "sample" as used herein is used in its broadest sense and includes environmental and biological samples.

Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods, which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence, which lacks even a partial degree of complementarity (e.g., less than about 30% identity); in the absence of non-specific binding, the probe will not hybridize to the second non-complementary target.

The terms "homology" and "homologous" as used herein in reference to amino acid sequences refer to the degree of identity of the primary structure between two amino acid sequences. Such a degree of identity may be directed to a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence that is a "homolog" is defined herein as an oligonucleotide sequence that exhibits greater than or equal to 50% identity to a sequence, when sequences having a length of 100 bp or larger are compared.

Low stringency conditions comprise conditions equivalent to binding or hybridization at 42° C. in a solution consisting of 5×SSPE (43.8 g/l NaCl, 6.9 g/l NaH2PO4.H2O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., CO t or RO t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. As indicated by standard references, a simple estimate of the Tm value may be calculated by the equation: Tm=81.5+0.41 (% G+C), when a nucleic acid is in aqueous solution at 1M NaCl. Anderson et al., "Quantitative Filter Hybridization" In: Nucleic Acid Hybridization (1985) [1]. Computations that are more sophisticated take structural, as well as sequence characteristics, into account for the calculation of Tm.

As used herein the term "stringency" is used in reference to the conditions of temperature, ionic strength, and the presence of other compounds such as organic solvents, under which nucleic acid hybridizations are conducted. “Stringency” typically occurs in a range from about Tm to about 20° C. to 25° C. below Tm. A “stringent hybridization” can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of “weak” or “low” stringency are used hybridization may occur with nucleic acids that are derived from organisms that are genetically diverse (i.e., for example, the frequency of complementary sequences is usually low between such organisms).

As used herein, the term “amplifiable nucleic acid” is used in reference to nucleic acids which may be amplified by any amplification method. It is contemplated that “amplifiable nucleic acid” will usually comprise “sample template.”

As used herein, the term “sample template” refers to nucleic acid originating from a sample that is analyzed for the presence of a target sequence of interest. In contrast, “background template” is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

“Amplification” is defined as the production of additional copies of a nucleic acid sequence and is generally carried out using polymerase chain reaction. Dieffenbach C. W. and G. S. Dveksler (1995) In: PCR Primer, a Laboratory Manual, Cold Spring Harbor Press, Plainview, N.Y. [2].

As used herein, the term “polymerase chain reaction” (“PCR”) refers to the method of K. B. Mullis U.S. Pat. Nos. 4,683,195 [3] and 4,683,202 [4], herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the “polymerase chain reaction” (hereinafter “PCR”). Because the desired amplified segments of the target sequence become the predominant sequences (in terms of concentration) in the mixture, they are said to be “PCR amplified”. With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term “primer” refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH).

The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term “probe” refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any “reporter molecule,” so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms “restriction endonucleases” and “restriction enzymes” refer to bacterial enzymes, each of which cut double-stranded DNA at or near a specific nucleotide sequence.

DNA molecules are said to have “5' ends” and “3' ends” because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the “5' end” if its 5' phosphate is not linked to the 3' oxygen of a mononucleotide pentose ring. An end of an oligonucleotide is referred to as the “3' end” if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being “upstream” or 5' of the “downstream” or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term “an oligonucleotide having a nucleotide sequence encoding a gene” means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc.

may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

The term "in operable combination" as used herein, refers to any linkage of nucleic acid sequences in such a manner that a nucleic acid molecule capable of directing the transcription of a given gene and/or the synthesis of a desired protein molecule is produced. Regulatory sequences may be operably combined to an open reading frame including but not limited to initiation signals such as start (i.e., ATG) and stop codons, promoters which may be constitutive (i.e., continuously active) or inducible, as well as enhancers to increase the efficiency of expression, and transcription termination signals.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., Science 236:1237 (1987) [5]. Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site. Sambrook, J. et al., In: Molecular Cloning: A Laboratory Manual, 2nd ed., Cold Spring Harbor laboratory Press, New York (1989) pp. 16.7-16.8. A commonly used splice donor and acceptor site is the splice junction from the 16S RNA of SV40 [6].

The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. Efficient expression of recombinant DNA sequences in eukaryotic cells involves expression of signals directing the efficient termination and polyadenylation of the resulting transcript. Transcription termination signals are generally found downstream of the polyadenylation signal and are a few hundred nucleotides in length.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: Molecular Cloning: A Laboratory Manual, Cold Spring Harbor Press, NY, pp 9.31-9.58 [6].

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J.

Sambrook, J. et al. (1989) supra, pp 7.39-7.52 [6].

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonuclotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes that encode products that control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences, such as promoters and enhancers, which control or influence the transcription of the gene. The 3' flanking region may contain sequences that direct the termination of transcription, posttranscriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., 3H, 1251, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837 [7]; 3,850,752 [8]; 3,939,350 [9]; 3,996,345 [10]; 4,277,437 [11]; 4,275,149 [12]; and 4,366,241 [13] (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 12 shows a gel where input RNA containing an xrRNA was challenged with Xrn1, RNase J1 (from bacteria), and Dxo1 (from yeast). All enzymes were expressed recombinantly and purified to high purity. RppH was included in all reactions to convert the 5' triphosphate to a monophosphate. This demonstrates that the xrRNA could be engineered to work in diverse hosts and have broad applicability.

DESCRIPTION OF THE INVENTION

Figure 1A:
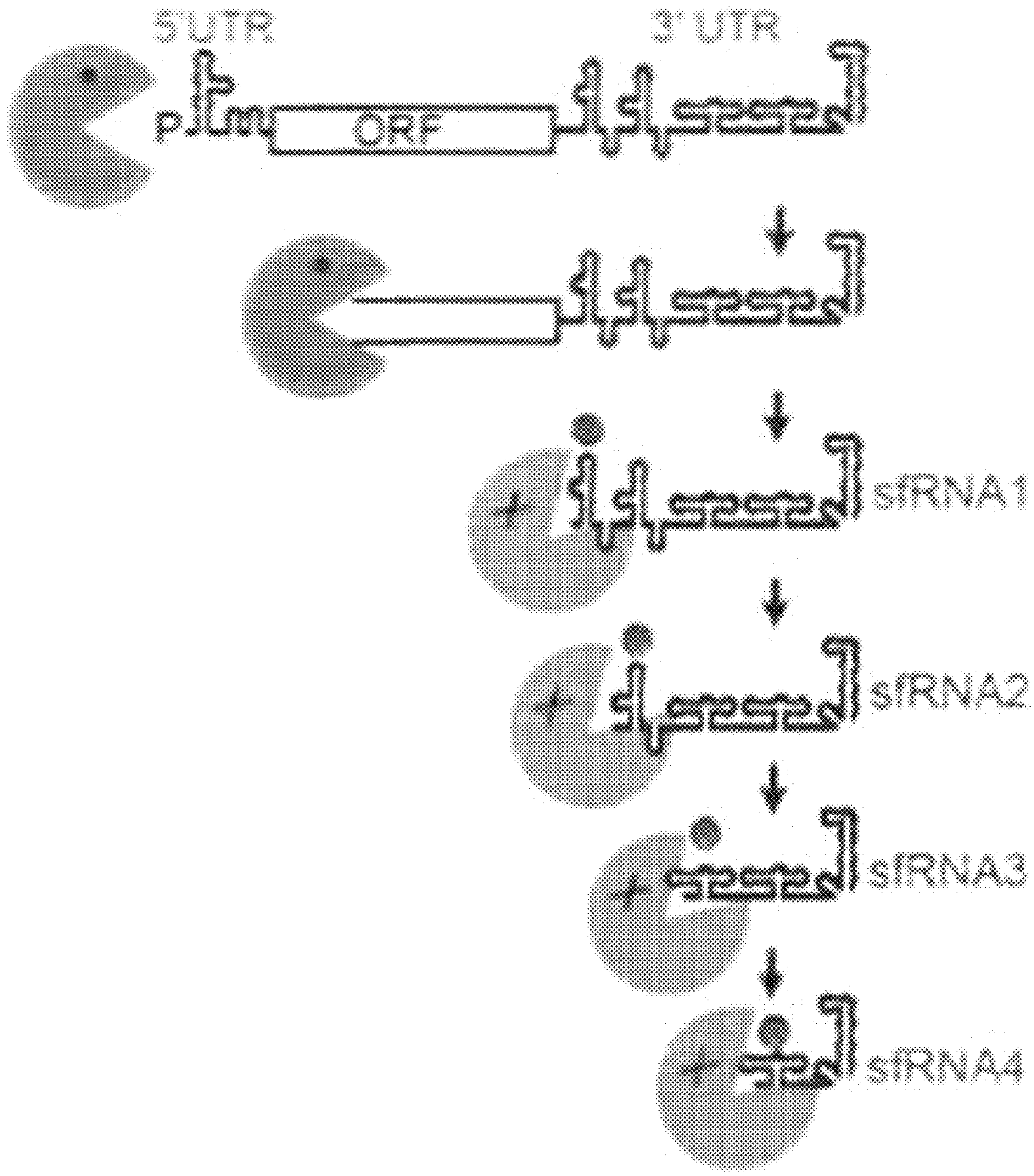
FIG. 1A shows xrRNA function. Xrn1 (green) loads on a FV RNA, degrades the RNA, then reaches a discrete 'xrRNA' structure in the 3' UTR and halts, leading to sfRNAs where Xrn1 appears to remain in an inactive state.

Flaviviruses are emerging human pathogens and worldwide health threats. During infection, pathogenic subgenomic flaviviral RNAs (sfRNAs) are produced by resisting degradation by the 5'→3' host cell exonuclease Xrn1 through an RNA structure-based mechanism wherein Xrn1-resistant flaviviral RNA, which contains interwoven pseudoknots within a compact structure that depends on highly conserved nucleotides [15]. The RNA's three-dimensional topology creates a ring like conformation, with the 5' end of the resistant structure passing through the ring from one side of the fold to the other. Disruption of this structure prevents formation of sfRNA during flaviviral infection. Thus, sfRNA formation results from an RNA fold that interacts directly with Xrn1, presenting the enzyme with a structure that confounds its helicase activity. The current invention envisions adapting creating similar RNA based interwoven pseudoknot structures to enable the preservation of and expression of targeted RNA transcripts.

Signal Activated RNA Interference

One reference, U.S. Pat. No. 9,029,524 [16], describes compositions and methods for signal activated RNA interference (saRNAi). The reference states that a pseudoknot is employed and may be resolved by the introduction of signal, such as a second polynucleotide. Unknotting of the pseudoknot may be accomplished when a signal polynucleotide binds to one of three regions on the signal-activated polynucleotide. In one example, the signal polynucleotide binds to the signal-detecting nucleotide and displaces the pseudoknotting strand from the stem-loop structure. This exposes the stem-loop structure to cleavage by Dicer and processing by the RISC complex. In a second example, the signal polynucleotide binds to the signal-detecting nucleotide at a region upstream of the pseudoknot, causing compression and steric/electrostatic repulsion between the signal-detecting strand and the stem-loop structure. The reference describes the polynucleotide structures as substantially resistant to endonucleases and exonucleases. The reference does not describe xrRNA sequences that contain a second heterologous sequence, nor does it describe the hybridization of two separate RNA molecules to form such an interwoven pseudoknot structure.

One reference, Chapman, E. G. et al. (2014), *Science* 344(6181), 307-310 [15], describes the structure of the sfRNA which halts the advance of the Xrn1 endonuclease via interruption of the Xrn helicase. The reference describes the crystallized structure of the sfRNA as containing interwoven pseudoknots that interrupt the structure through sequence changes, and halts the effectiveness of Xrm1. The RNA sequences described are sections of naturally occurring xrRNA and those that were engineered to evaluate the sequence's effectiveness against Xrn1. The reference concludes that the xrRNA structure is braced against the enzyme, holding the leading edge of the relevant RNA duplex behind the concave ring structure and away from these helices, suggesting a mechanism for RNA structure-driven Xrn1 resistance and, by extension, sfRNA production. The reference does not describe xrRNA sequences that contain a second heterologous sequence, nor does it describe hybridization of two separate RNA molecules to form such an interwoven pseudoknot structure.

One reference, Chapman, E. G. et al. (2014), *eLife* 3, e01892 [17], describes modification of sfRNA to evaluate the sequence and structural features of the RNA that conferred resistance to the Xrn1 endonuclease. The reference concludes that disruption of the lead sequences of sfRNA leads to the elimination of disease related sfRNAs, thus linking the RNA structure to sfRNA production. The reference states that such Xrn1-resistant activity resides in discrete and portable structural elements, the RNA sequences. The reference does not describe xrRNA sequences that contain a second heterologous sequence, nor does it describe the hybridization of two separate RNA molecules to form such an interwoven pseudoknot structure.

One reference, Kieft, J. S. et al. (2015), RNA Biol. E-published Sep. 23, 2015 [18], describes that continued analysis and interpretation of the structure of sfRNAs reveals that the tertiary contacts that knit the xrRNA fold together are shared by a wide variety of arthropod-borne FVs, conferring robust Xrn1 resistance in all tested. The reference further discloses that some variability in the structures that correlates with unexplained patterns in the viral 3' UTRs. The references' examination of these structures and their behavior in the context of viral infection leads to a new hypothesis linking RNA tertiary structure, overall 3' UTR architecture, sfRNA production, and host adaptation. The reference does not describe xrRNA sequences that contain a second heterologous sequence, nor does it describe the hybridization of two separate RNA molecules to form such an interwoven pseudoknot structure.

One reference, Moon, S. L. et al. (2012), RNA 18(11), 2029-2040 [19], describes an evaluation of sfRNAs, including several experiments introducing sfRNA sequences downstream from a reporter GFP-expressing construct (e.g., a heterologous sequence). In part, this was done to evaluate the decay curves for mRNA in correlation with the amount of sfRNA present in a cell. These experiments further establish the relationship of sfRNA with XRN1 depletion and mRNA transcript stability. The reference states that pseudoknots and related structures have been shown in the past to hinder the action of other enzymatic complexes that move directionally along RNA and that pseudoknots can serve as roadblocks for ribosomes and influence frameshifting rates. The reference does not describe sfRNA sequences upstream of heterologous RNA. The reference does not describe xrRNA sequences that contain a second heterologous sequence, nor does it describe the hybridization of two separate RNA molecules to form such an interwoven pseudoknot structure.

One reference, Burke, D. H. et al. (1996), *J. Mol. Biol.* 264(4), 650-666 [20], describes several RNA inhibitors of HIV-1 RT that differ significantly from the pseudoknot ligands found previously, along with a wide variety of pseudoknot variants. Patterns of conserved and covarying nucleotides yielded structural models consistent with 5' and 3' boundary determinations for these molecules. Among the four isolates studied in detail, the first is confirmed as being a pseudoknot, albeit with substantial structural differences as compared to the canonical pseudoknots identified previously. The second forms a stem-loop structure with additional flanking sequences required for binding. The minimal fully active truncations of each of these four isolates compete with each other and with a classical RNA pseudoknot for binding to HIV RT, suggesting that they all recognize the same or overlapping sites on the protein, in spite of their apparently dissimilar structures. The reference does not describe xrRNA sequences that contain a second heterologous sequence, nor does it describe the hybridization of two separate RNA molecules to form such an interwoven pseudoknot structure.

One reference, U.S. Pat. No. 5,256,775 [21], describes making 3' and/or 5' end-capped oligonucleotides so as to render the oligonucleotide resistant to degradation by exonucleases. The exonuclease degradation resistance is provided by incorporating two or more phosphoramidate and phosphorocmonothioate and/or phosphorodithioate linkages at the 5' and/or 3' ends of the oligonucleotide, wherein the number of phosphoramidate linkages is less than a number which would interfere with hybridization to a complementary oligonucleotide strand and/or which would interfere with RNAseH activity when the oligonucleotide is hybridized to RNA. The reference does not describe xrRNA sequences or interwoven pseudoknots, nor does it describe the hybridization of two separate RNA molecules to form such an interwoven pseudoknot structure.

One reference, U.S. Patent Application Publication Number US 2014-0329880 A1 [22], describes exonuclease resistant polynucleotides with a 5' end and a 3' end and comprises a blocker domain having a non-nucleic acid polymer segment and a phosphorothioate segment. The reference also describes exonuclease resistant duplex polynucleotide having a length of about 17 to about 30 bp and comprising a guide strand complementary bound to a passenger strand, each of the guide strand and passenger strand having a 5' end and a 3' end, the duplex RNA having at least one configuration allowing processing of the guide strand by dicer and/or an argonaute enzyme, the passenger strand comprising the exonuclease resistant polynucleotide herein described, in a configuration in which the second end of non-nucleic acid polymer is presented at the 5' end of the passenger strand. In some embodiments, the exonuclease resistant duplex polynucleotide is a targeting domain. The reference does not describe xrRNA sequences or interwoven pseudoknots, nor does it describe the hybridization of two separate RNA molecules to form such an interwoven pseudoknot structure.

Various Embodiments

In one embodiment, the invention contemplates various applications of RNA sequences derived from the genomic RNA of flaviviruses (FVs). These derived RNA sequences have been found to be resistant to cell enzyme Xrn1, the dominant cytoplasmic 5'→3' exonuclease. These discrete Xrn1-halting sequences are referred to as "Xrn1-resistant RNAs" (xrRNAs). The xrRNAs have been found to have distinct structural elements and further have certain conserved sequences to retain these resistant structural elements.

In one embodiment, the invention contemplates that such sequences of RNA could be useful in a number of applications including, but not limited to: A) introduction of an xrRNA sequence "in cis" upstream of desired heterologous mRNA sequences to improve the half-life of the heterologous mRNA sequences from exonuclease degradation; and B) provide Xrn1 nuclease resistance by the "in trans" association of an RNA that provides Xrn1-halting ability to an RNA that does not have this ability, thus protecting a "target" RNA from degradation by hybridization of a "protecting" RNA. In this approach, structures similar to xrRNAs could be generated by the hybrid association of two heterologous RNAs rather than placing an xrRNA sequence on at least one heterologous RNA sequence.

In one embodiment, the invention contemplates that the "in trans" configuration could be used: (1) to alter specific endogenous RNA degradation rates within cells as a "transcriptome editing" tool and (2) coupling such RNA combinations with a way to turn protected (but uncapped or decapped) mRNAs into viable translation templates as a "translatome editing" tool. It is believed by adjustment of the RNA sequence, that the "protecting RNA" could be "tuned" to achieve various protection levels and translation levels of endogenous RNAs.

DETAILED DESCRIPTION OF THE INVENTION

The technology/inventions described here are based on our discoveries regarding a viral RNA that has the extraordinary ability to block a powerful cellular exonuclease. This RNA structure is thought to be critical to the virus, but the current invention has now enabled the removal of the RNA structure from that context and engineer it as a manipulator of cellular processes.

Figure 1B:
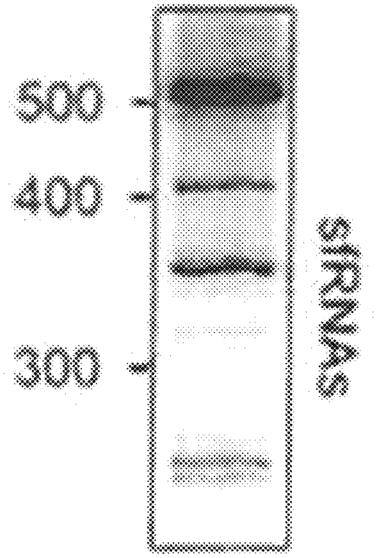
FIG. 1B shows the pattern of sfRNA production in West Nile Virus (Northern blot).
Figure 1C:
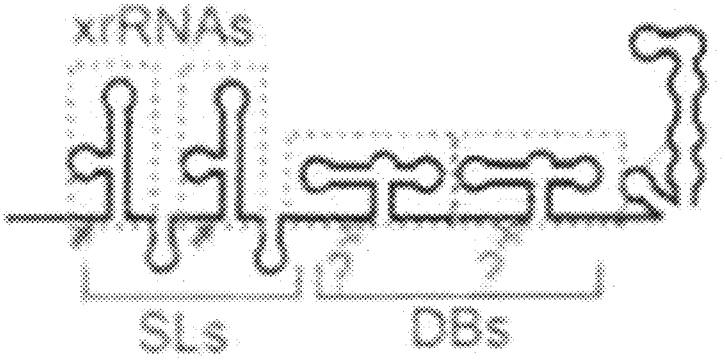
FIG. 1C shows 3'UTR organization, red arrows are known or putative Xrn1 halt sites. Known or putative xrRNAs are boxed. Although depicted as separate entities, their functions may be coupled. SLs=stem loops, DB=dumbbells.
Figure 2:
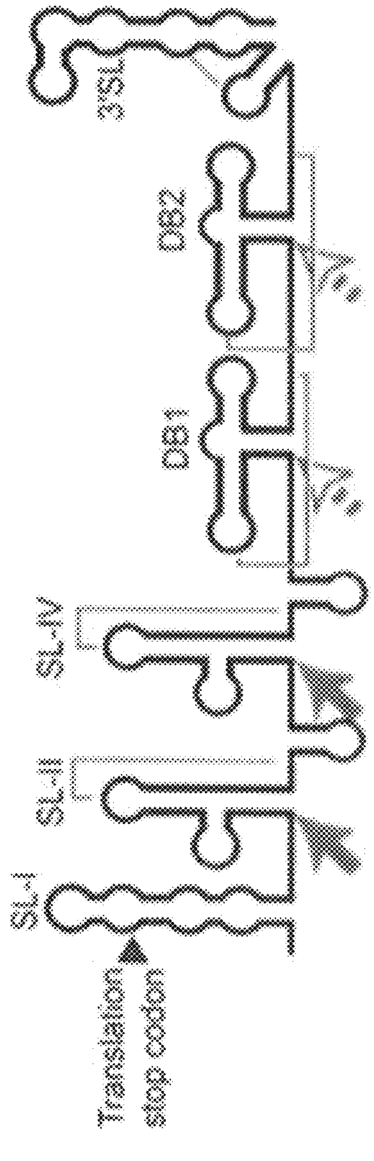
FIG. 2 depicts the basic architecture of a FV 3' UTR and proposed halt sites for Xrn1 (DENV2 shown as a representative example). The halt sites and structures of the 'SL' motifs (solid arrows) have been characterized; the halt sites and structures of the 'DB' motifs remain unexplored (open arrows). Dashed lines indicate likely PK interactions.

Initial studies were focused on the ability of flaviviruses (FVs) to use RNA structure to resist degradation by Xrn1, a powerful cellular exonuclease. Briefly, during replication of arthropod-borne FVs, copies of the viral genomic RNA are made. Infection also leads to a set of discrete shorter flaviviral RNAs that accumulate to high levels [23-25]. These subgenomic flaviviral RNAs (sfRNAs) are ~200-500 nt in length and are directly linked to viral cytopathicity in cultured cells (mammalian and insect) and for disease symptoms in fetal mice [26-28]. The sfRNAs are made by partial digestion of FV genomic RNA by host cell enzyme Xrn1, the dominant cytoplasmic 5'→3' exonuclease (FIG. 1) [27]. In normal cellular metabolism, Xrn1 recognizes the 5' monophosphate of decapped mRNAs and catalyzes their degradation in a 5' to 3' directional process [29]. In FV infection, Xrn1 loads on some presumably decapped copies of the viral RNA genome and degrades them in a 5'→3' process until it halts at defined locations in the 3'UTR, resulting in the set of sfRNAs [26-28]. This mechanism is surprising given Xrn1's ability to degrade stable structured RNAs such as ribosomal RNA. These discrete Xrn1-halting elements are referred to as “Xrn1 resistant RNAs” (xrRNAs)[17]. An FV xrRNA has been characterized, that being the stem-loop (SL) type often found in tandem near the 5' end of FV 3'UTRs [26-28] (FIG. 2). The functional, biochemical, structural, and virological studies included the first high-resolution three-dimensional structure of a functional SL-type xrRNA (solved by crystallography). It was found that these RNAs adopt a specific three-dimensional fold, and there is a suggested mechanism for how these RNAs stop progression of Xrn1 using a combination of thermodynamic stability coupled to a unique fold that mechanically confounds the helicase activity of Xrn1. This characterization of these RNAs has revealed how novel and remarkable they are; the structure is unlike anything previously found. These discoveries were published in 2014 in Science and eLife, the contents of which are incorporated herein by reference [15, 17].

These discoveries have provided an insight into the function of these xrRNAs and also inspired the current invention ideas for how they could be used as tools, potentially as part of novel therapeutic strategies in which stabilizing RNAs within a cell is important. In other words, no way is known wherein a specific RNA within a cell can be super-stable, perhaps evading the degradation machinery completely and remaining a viable, biologically active RNA. The xrRNAs may provide the basis for creative engineering and inventions that would allow this type of precise control within living cells. The current invention engineers and explores this possibility.

Figure 3:
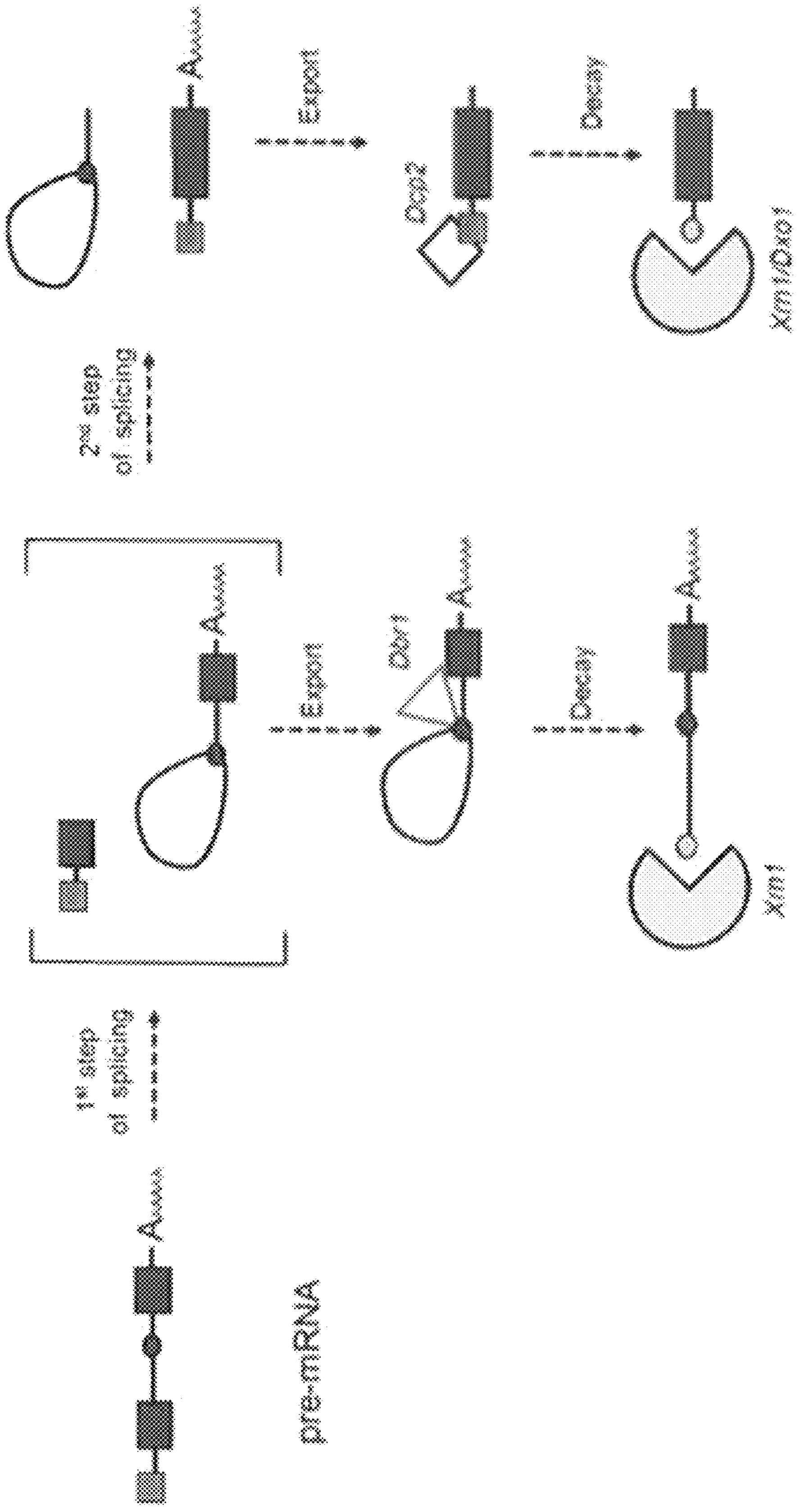
FIG. 3 depicts splicing and decay pathway in yeast. Both fully spliced mRNAs and splice defective pre-mRNA intermediates are degraded by Xrn1
Figure 4A:
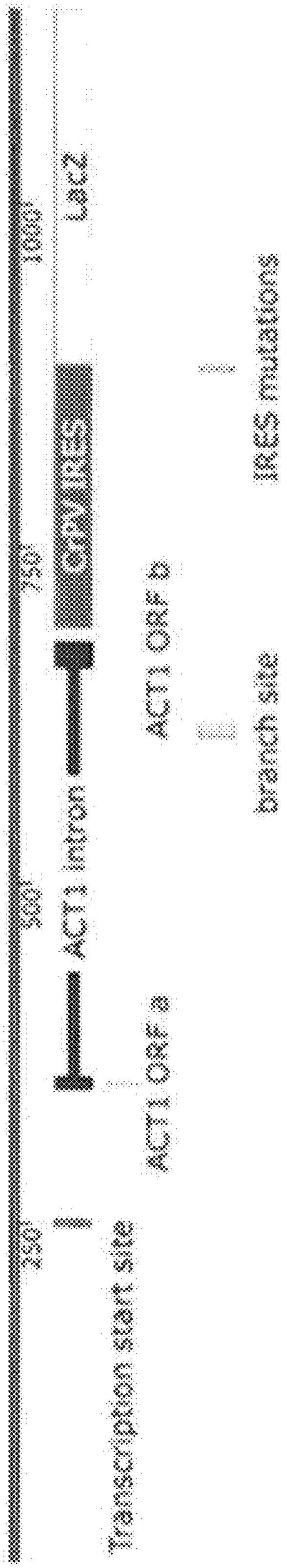
FIG. 4A shows the design of reporter transcript with a cricket paralysis virus (CrPV) IRES, but no xrRNAs.
Figure 4B:
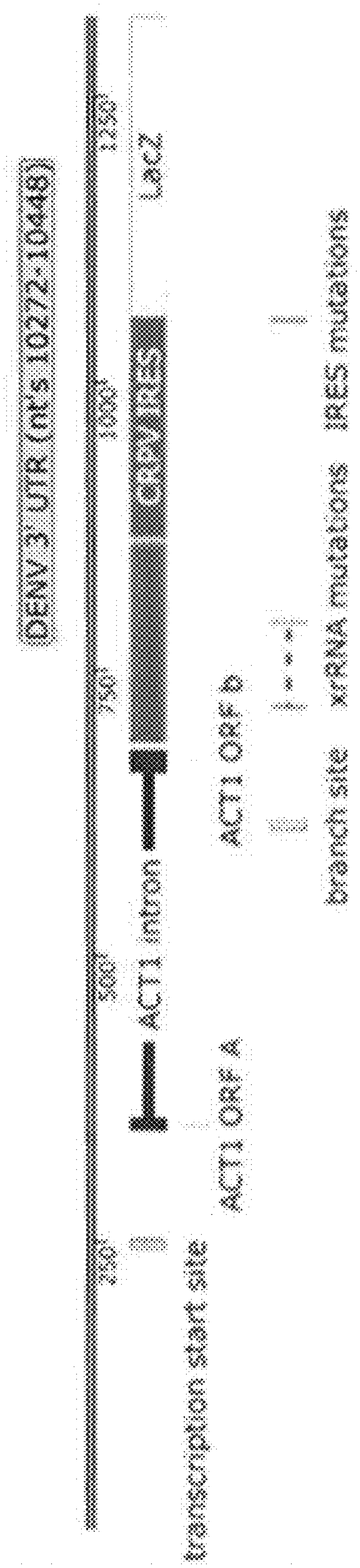
FIG. 4B shows version of this transcript with xrRNAs (wavy lines) inserted. Transcripts were constitutively transcribed from 2-micron plasmids in budding yeast.
Figures 5A, 5B:
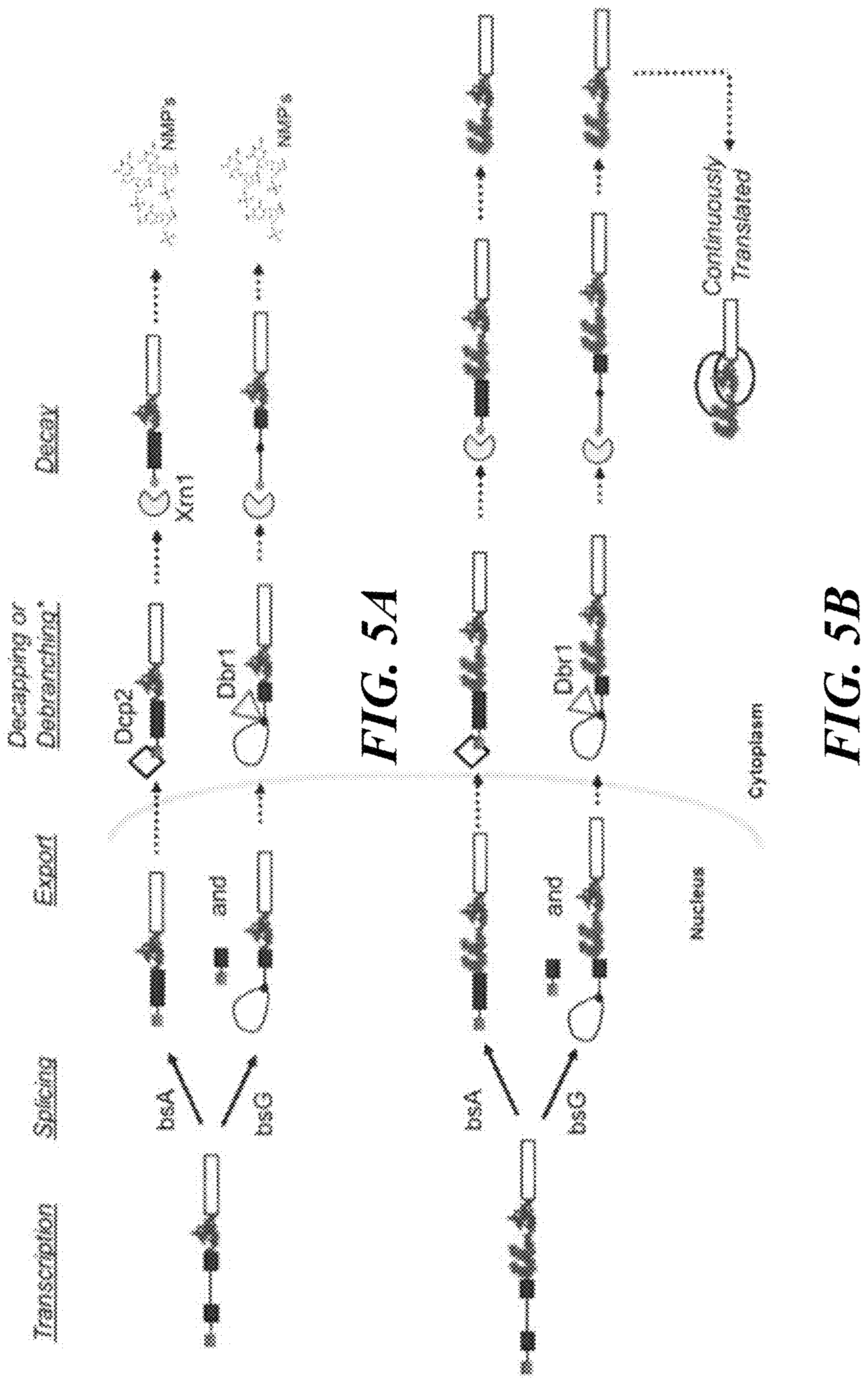
FIG. 5A depicts the pathway from transcription to degradation for transcripts from the non-xrRNA-containing RNAs.
FIG. 5B depicts the Pathway for the transcripts containing xrRNAs (red). Although both contain an IRES (blue) and can produce protein, it was expected that the mRNAs without the xrRNA to be degraded more quickly and produce less protein, while those with the xrRNAs should be protected from degradation and produce more protein.

Demonstration that Flavivirus-Derived xrRNAs can Resist Xrn1 in Living Cells to Protect Functional mRNAs Characterization of these xrRNAs demonstrated that they appear to be modular structure elements. That is, the current invention hypothesizes that one could remove an xrRNA sequence from its native context in the viral genomic RNA and place it within any other RNA, and thus protect any downstream sequences from degradation by Xrn1. If true, one could then extend the lifetime of any RNA in the cell in which this element was installed. To test this, the Xrn1-mediated decay process in yeast was chosen as a tractable model system (FIG. 3). A vector that would drive expression of an mRNA was created containing (from 5' to 3'): leaders sequence, the ACT1 intron, a viral internal ribosome entry site (IRES), and a LacZ reporter sequence (FIG. 4A). The viral IRES was included because partial digestion of the mRNA by Xrn1 may give rise to a stable, but uncapped message that would not be used in translation; the IRES allows translation to occur internally, downstream of the xrRNAs. Thus, in this mRNA two viral RNA structures from different viruses have been coupled. Expression of this mRNA in yeast may give rise to a spliced and capped RNA that would serve as the template for producing the reporter proteins at some level, and would also be subject to degradation at some rate (FIGS. 5A & B). To test the function of the xrRNAs, the two “tandem” xrRNAs from Dengue virus were installed into this reporter construct between the intron and the IRES (FIG. 4B). If the xrRNAs protect the message from Xrn1 degradation, one might expect an accumulation of partially degraded mRNAs that should be able to produce enzyme, driven by the action of the IRES (FIGS. 5A & B).

Figure 6:
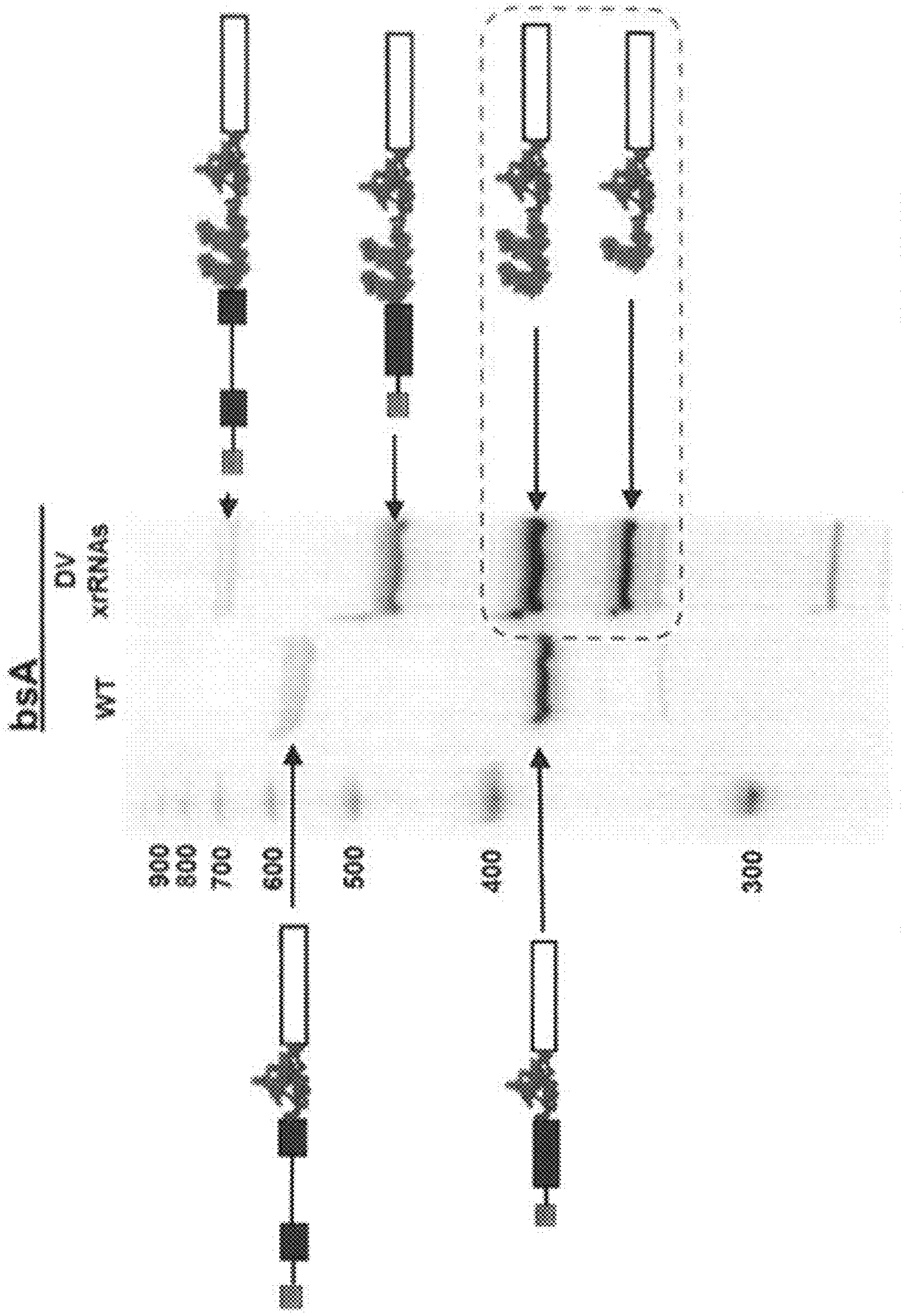
FIG. 6 shows Protection of translationally competent mRNAs in budding yeast. Blue denotes the CrpV IRES, red denotes the tandem copies of xrRNA. The open box is the open reading frame encoding the enzyme. The lanes are explained in the text. The dashed box indicates the products that build up because Xrn1 cannot degrade past the xrRNAs.
Figure 7:
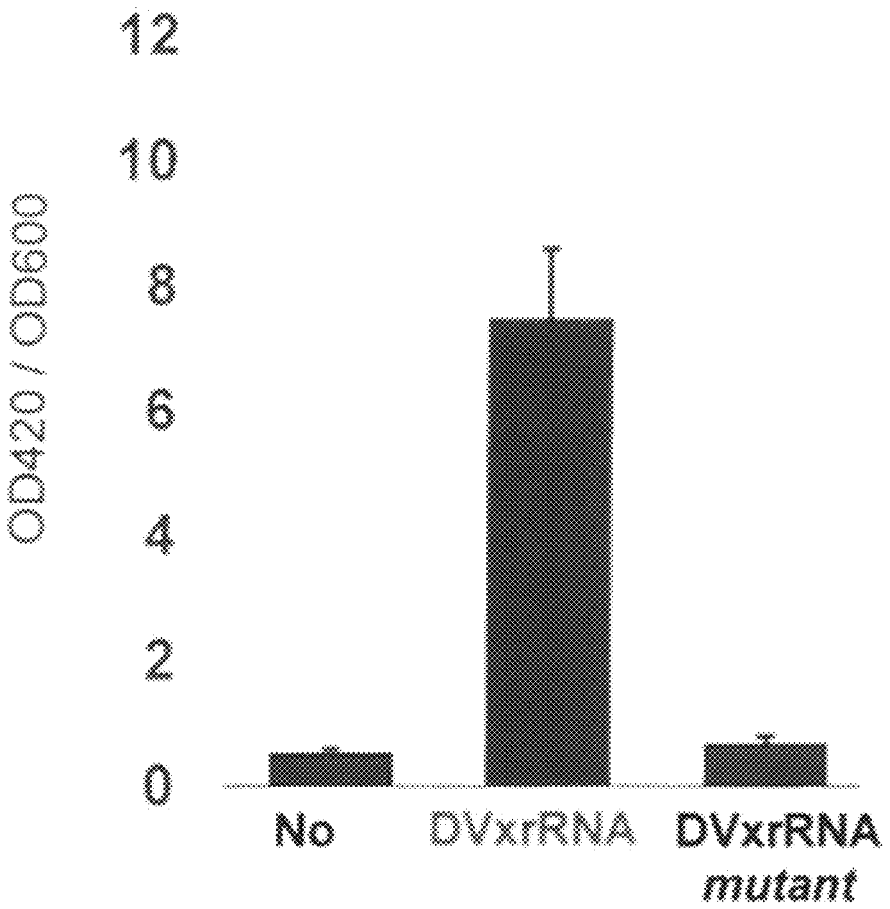
FIG. 7 shows an activity assay to measure B-galactosidase (LacZ) levels made from mRNAs produced in budding yeast. LacZ activity is reflected by an increase in ONPG hydrolysis (OD420) per cell (OD600). Including the xrRNAs leads to an increase in the amount of LacZ activity, demonstrating that the xrRNA-protected mRNA is competent for IRES-dependent translation. Mutation of the xrRNAs returns LacZ activity to the level of mRNAs without any xrRNAs. This increase in protein is due to the accumulation of the RNA products boxed in FIG. 6. These uncapped, partially degraded, but protected mRNAs are functional templates for translation.

This experiment was successful, and is shown in FIG. 6 and FIG. 7.

This idea was also used to test the Dbr1/Xrn1-mediated decay of splice-defective pre-mRNA intermediates and found results that are consistent with the above.

The important conclusions: 1) The xrRNAs from flaviviruses are modular elements that may be placed in a non-native contex1 where they retain function. 2) In living cells that differ from those they evolved in, these xrRNAs halt Xrn1 and protect downstream RNA. 3) The protected RNAs are competent as templates for translation, in this case using an IRES placed downstream of the xrRNAs.

These results suggest that xrRNAs may be used as powerful genetic tools to artificially ex1 end the lifetime of any arbitrary RNA within a living cell. If placed within an mRNA, they may protect anything that is 3' of them, and other RNA elements can be engineered with the xrRNAs to achieve specific outcome. This could be achieved using modern genomic editing tools such as CRISPR to install these engineered elements in any RNA in a cell. It is believed that currently, there is no existing way to extend the lifetime of a specific arbitrary RNA in cells. Although this method has only been tested in yeast, the fact that xrRNAs work in both insect and mammalian cells during flavivirus infection suggests that they may in fact be “universal” Xrn1 blockers. Furthermore, the IRES used in these studies has been shown to function in diverse systems, including human cells, yeast, rabbit reticulocyte lysate, bacteria, wheat germ extract, insects, etc. Hence, this may be a widely applicable method.

Demonstration that Xrn1 Resistance can be Achieved by in Trans Association of Two RNAs.

Figure 8A:
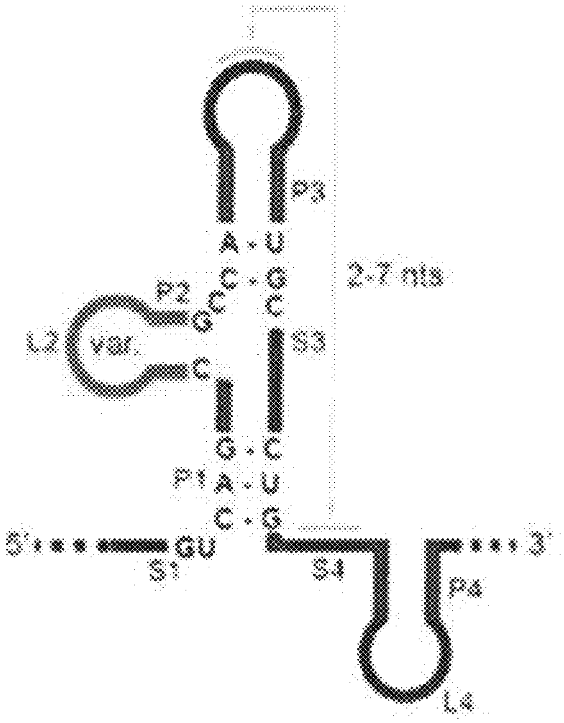
FIG. 8A depicts a secondary structure cartoon of an xrRNA. The nucleotides explicitly shown are conserved in all xrRNA we have studied so far. The secondary structural elements are labeled. The P2/L2 stem loop is variable between xrRNAs and we have mutated it without affecting function.
Figure 8B:
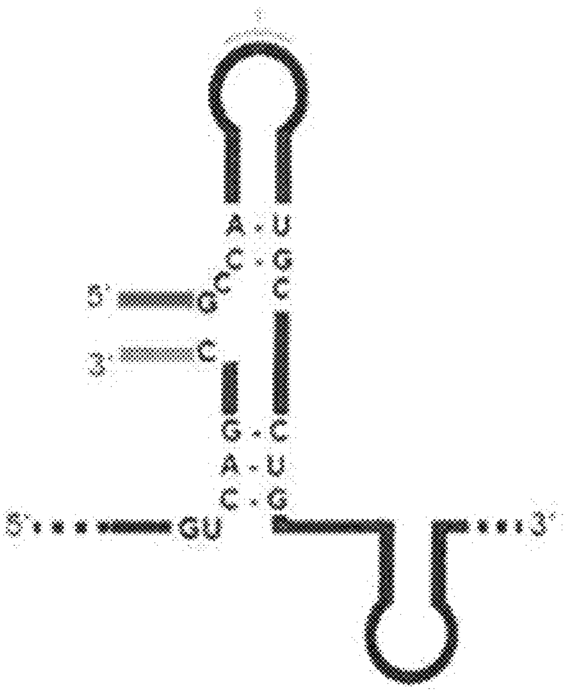
FIG. 8B depicts a hypothesized L2 loop as a location where the xrRNA could be split into two pieces (bottom left sequence and top and right sequence).
Figure 8C:
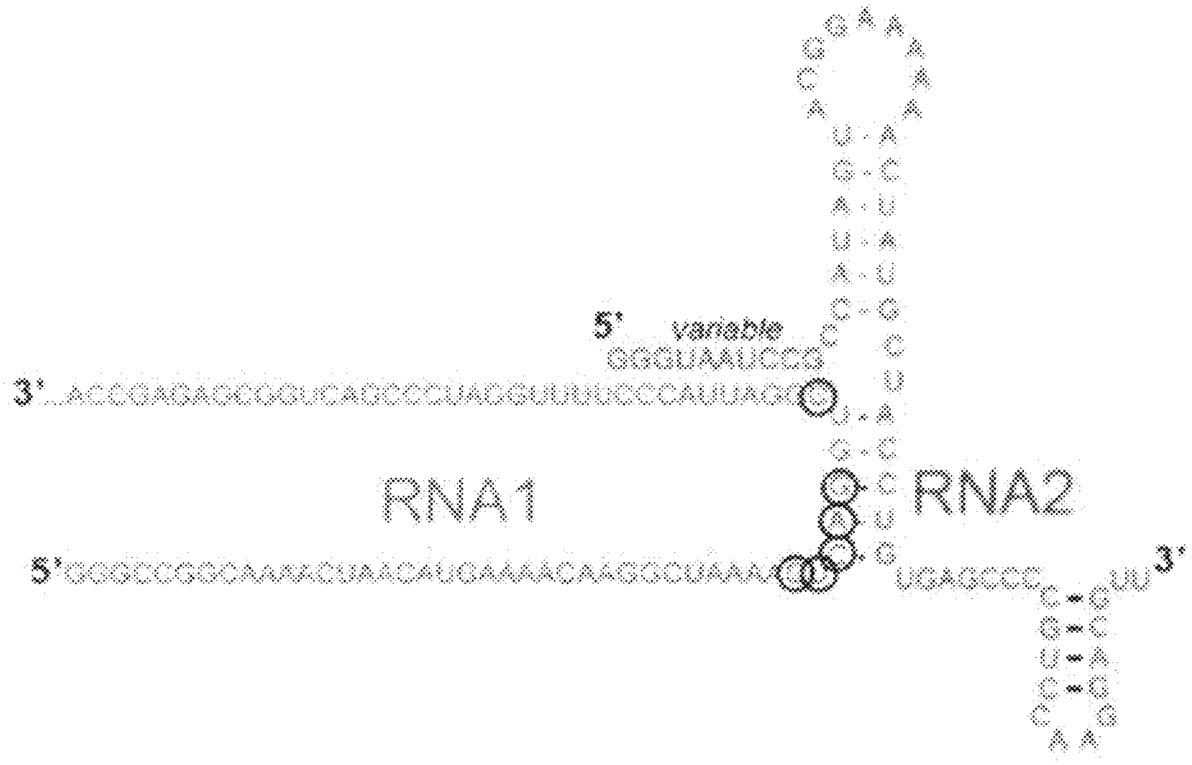
FIG. 8C depicts RNAs used to test this idea. RNA1 (SEQ ID NO:1) is the "substrate" which is recognized by the 5' complementary sections of as second RNA sequence (RNA2), which is the "protector". In theory, RNA 1 could be any length, because RNA2 (SEQ ID NO:2) must only base pair to it as shown. The part labeled as "variable" can be changed to recognize different sequences. The circled nucleotides limit what sequences may be recognized (at this point), but might be varied with more engineering of the RNA.
Figure 8D:
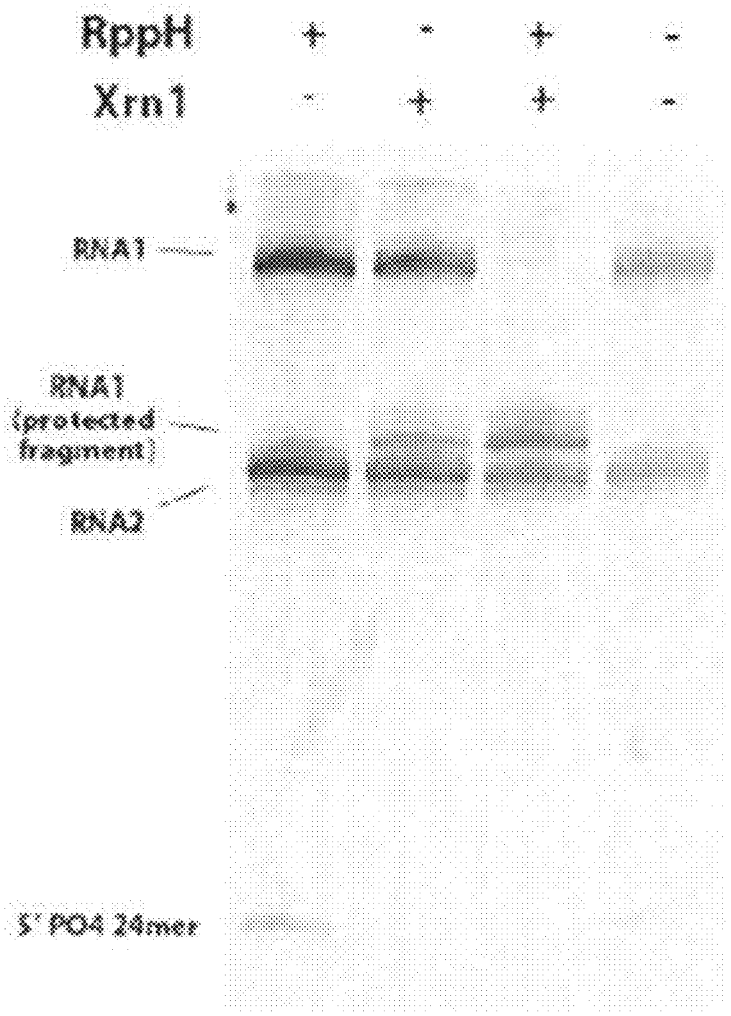
FIG. 8D show the result of a resistance assay. RNA1 is processed to a shorter product, but is not fully degraded by Xrn1 when RNA2 is present.

The results described above show that the xrRNAs could be a powerful genetic tool. In the manifestation described in section II, the xRNA was placed within the RNA to be protected (i.e. placed in cis). This is useful, but the power of the xrRNAs could be extended if they could somehow be used in a method in which one RNA could protect another RNA in trans. Towards this end, the published crystal structure of an xrRNA was examined and published biochemical characterization results also considered [15, 17]. These data show that loop L2 of the xrRNA structure may be mutated without functional affect, and the P2 stem that this loop caps may be shortened, lengthened, or altered without losing the ability to halt Xrn1 (FIGS. 8A & B). It was therefore reasoned that one could split the xrRNA into two pieces: a “target” strand (RNA1) and a “protecting” strand (RNA2). It was hypothesized that in the absence of RNA2, RNA would be rapidly degraded by Xrn1, but when RNA2 was added, it would anneal to RNA1, induce a fold, and protect RNA1 from degradation (FIG. 8C). This idea was tested using the established in vitro system with purified Xrn1 (FIG. 8D). As hypothesized, RNA1 (SEQ ID NO:1, GGGCCGGCAAAACUAACAUGAAAACAAGGC-UAAAAGUCAGGUCGGAUUACCCUU UUG-GAUCCCGACUGGCGAGAGCCA) was able to protect by addition of RNA2 (SEQ ID NO:2, GGGUAAUCCGCCAU-AGUACGGAAAAAACUAUGCUACCUGUGAGCCCC-GUCC AAGGACGUU), demonstrating the current invention idea of engineering the xrRNA to operate as an in trans protector is a valid approach. This result shows that the current invention may be an RNA-based on an xrRNA, which offers in trans protection to other RNAs from degradation by Xrn1. Such an RNA has not been discovered in nature.

The potential uses and implications of this invention are many. Currently, it has been shown that this system works in vitro. If the RNA can be shown to work in the complex environment of living cells, one could have a way to protect endogenous, unmodified RNAs from degradation within a cell. This is exciting, because mRNA-based therapeutics are being actively pursued by several entities, but one limitation/challenge they face is the stability of the therapeutic mRNAs. In addition, one might be able to increase the levels of desirable mRNAs such as antitumor-encoding mRNAs or even noncoding RNAs with desirable effects, without having to alter the genome. As CRISPR is a genome-editing tool, the technology of the current invention could be a transcriptome-editing tool.

Development of "in Trans" Protection of RNA Method

The creation of an "in trans" protection system in vitro described herein is exciting, but additional value lies in:

(1) Using the current invention system in more complex environments to alter specific endogenous RNA degradation rates within cells as a "transcriptome editing" tool.

(2) Coupling it with a way to turn protected (but uncapped) mRNAs into viable translation templates as a "translatome-editing" tool.

Steps for achieving this and for simultaneously developing additional in vitro and in vivo tools are described below.

Step 1: Demonstrate that in trans protection can yield a stable message that is a substrate for translation in lysate, using an IRES installed within the mRNA. This is similar to what was done in yeast, except the xrRNA will not be installed in the message; rather protection will be provided in trans.

Step 2: Develop a way to provide the signal to initiate translation in trans, coupled to the protecting RNAAn endogenous cellular mRNA has no IRES, and thus partial degradation by Xrn1 would not yield a viable template for translation. However, some plant viruses use a discrete structure in their 3' untranslated regions that binds the cap-binding protein elF4E without using a cap. This structure is brought to the 5' end of the plant viral RNA by base-pairing, and this leads to translation initiation (FIG. 9) [30]. Hence, nature has provided a translation initiation element that we may exploit to be used in trans. It is thought that by coupling this to the current xrRNA invention, one may produce a single RNA that can protect another RNA in trans AND drive its translation.

Step 3. Test functionality in living cells. The above ideas (steps 1 and 2) can first be tested in a cell-free, translationally competent lysate using added Xrn1. Once success is achieved in these systems, the functionality of these RNAs will be tested by transfecting them or expressing them in human cell culture, targeting various endogenous mRNAs. If one could add an RNA to a cell, extend the lifetime of a specific RNA this would be very powerful (the opposite of siRNAs or shRNAs), this would be a novel method of broad usefulness. If the RNA is an mRNA, and one can drive it to be translated, this would also be very powerful. Achieving this would be a major leap, with consequences for both research tools and therapeutics.

Step 4. Extend the RNA targets that can be affected by xrRNAs. Currently, the potential use of the in trans protection method is limited by the fact that the "protecting RNA" only can pair to a certain sequence in the target RNA; thus, this sequence must be naturally found in the endogenous RNA This sequence is not overly constraining (for example, the P53 5' leader contains it) but does limit use. Thus, efforts could be made to engineer the protecting RNA through several strategies (including characterizing additional viral xrRNAs and in vitro selection methods) to expand the list of targets.

Step 5. "Tune" the "protecting RNA" to achieve various protection levels and translation levels of endogenous RNAs.

Although each of these steps are in progress, they represent an intellectual leap in taking an RNA found in the 3' end of flaviviruses and using it to develop a tool that can be used to protect an arbitrary RNA in a cell from degradation by Xrn1, driving its translation (if desired), and doing so in a tunable way with no need to overexpress the target RNA or edit the genome.

xrRNAs could be Controlled by Small Molecules

Figure 10:
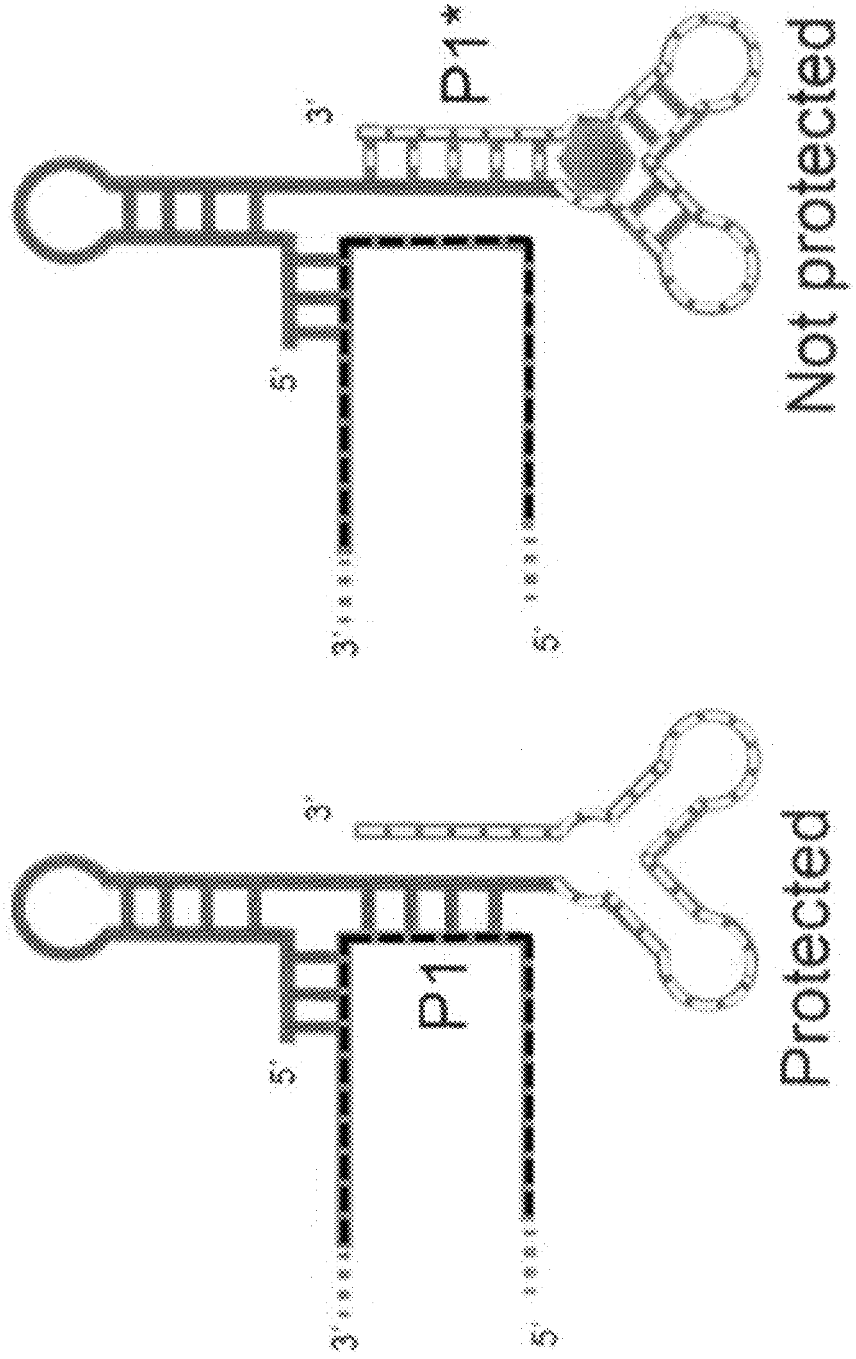
FIG. 10 shows a strategy to control Xrn 1 resistance using a small molecule. In this particular example, the "protecting RNA (solid) has a G-box riboswitch appended to its 3' end (light dashed line), with a sequence that can compete for helix P1 that is formed when the protecting RNA hybridizes to the substrate RNA (dark dashed line). Upon binding of the small molecule (block with SM; in this case, hypoxanthine or other related ligands) the riboswitch folds and helix P1''' forms. This disrupts the •P1 helix and the protector" RNA no longer can halt Xrn1 from degrading the substrate.

An additional level of functionality to the above-described method could be achieved if the protecting function was controllable by the action of a small molecule. This could be achieved in both the "in cis" or "in trans" xrRNAs. To develop this, two next steps are envisioned:

Step 1. Demonstrate the ability to couple an xrRNA to a riboswitch. Riboswitches are metabolite-sensing RNAs that change their fold depending on the binding off the small molecule metabolite. They could be used to create a small molecule sensing xrRNA, one way that is likely to work (a purine-sensing riboswitch [31]) is shown in FIG. 10. The use of riboswitches might allow coupling of a given mRNA's abundance to metabolite concentrations.

Figure 9:
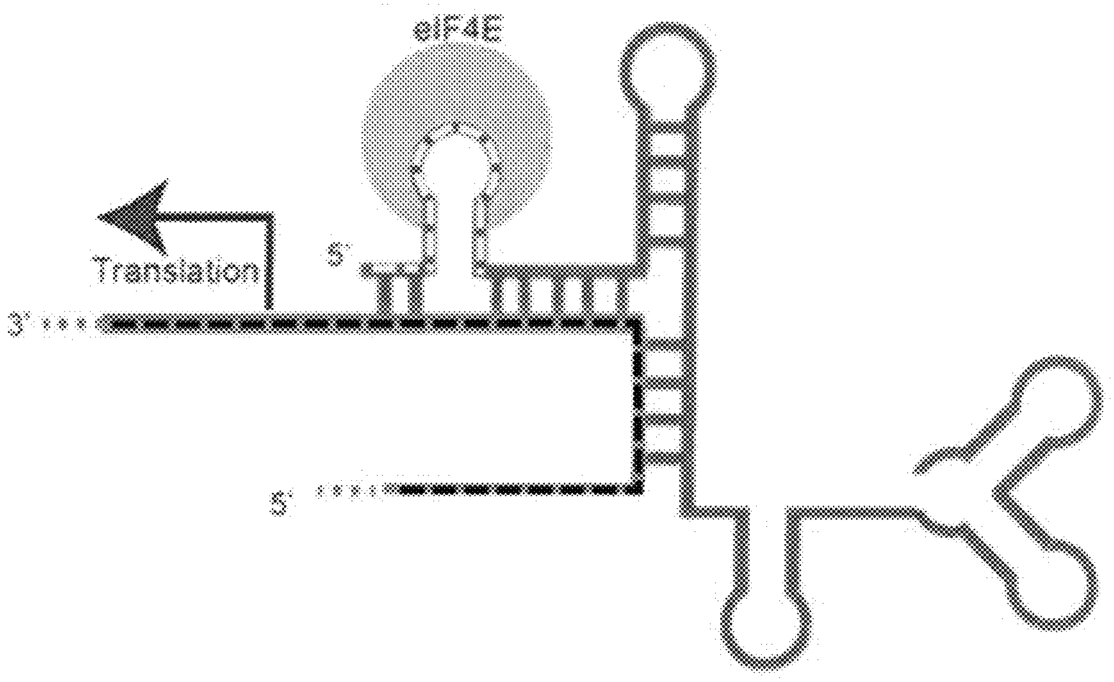
FIG. 9 shows a cartoon representation of a highly modified engineered xrRNA based RNA, The red is the portion that base pairs to any target mRNA in the cell (dark dashed line) and protects it from degradation. In light dashed lines is a plant viral RNA sequence that recruits the cap binding protein (round green ball) and drives translation of the protected RNA. In dark line on the 3' end is another RNA structure; it could be a protein binding site, an aptamer, a Spinach-RNA for visualizing this RNA in the cell, etc.

Step 2. The use of riboswitches to control xrRNA function is useful, but for many applications is limited because ultimately there is a desire to control the xrRNA with a small molecule that is NOT an endogenous metabolite. Selection-based, directed evolution-type methods can help achieve this. The example shown in FIG. 9 is a proof of principle; long-term engineering could yield version capable of responding to a set of small molecules either positively or negatively.

xrRNAs could be Used to Simultaneously Protect RNA and Deliver "Cargo"

Figure 12:
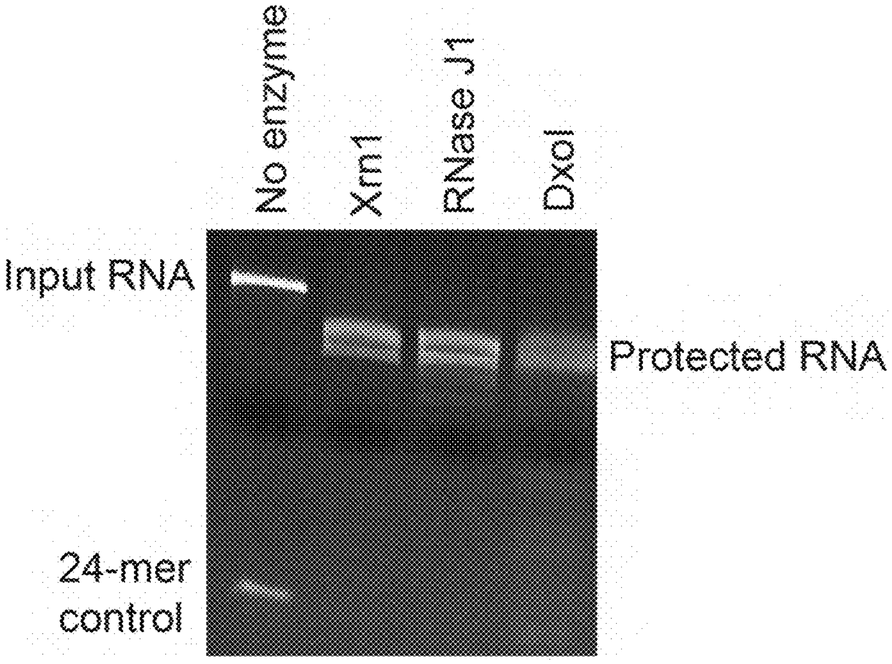
FIG. 12 shows that Xrn1 resistant RNAs from flaviviruses can resist degradation by different exonucleases.

The fact that the P2/L2 stem-loop in an xrRNA can be altered extensively without functional consequence suggests that this could be a place to install specific RNA sequences as "cargo" that would be delivered with the xrRNA. Likewise, the 5' or 3' ends of the RNA could be used to attached additional cargo (as with the elF4E binding element mentioned above). For example, a protein-binding sequence could be placed there, or "Spinach" sequence [32, 33], or even perhaps a short open reading frame (FIG. 9). Cargo could also be attached to the 3' end of the protecting RNA, which is not necessary for protection from Xrn1. In this way, an RNA could be protected and coupled with delivery of a specific RNA structure or functional element. In its most dramatic manifestation, an entire open reading frame could be placed as cargo, and combined with small-molecule dependent control (for example) unique tools created.

xrRNAs could be Used to Block Diverse Exonucleases and Affect RNA Levels in Several Domains of Life Flaviviruses infect eukaryotes and the xrRNAs have evolved to resist progression of Xrn 1. However, it was reasoned that they might function by forming a general mechanical unfolding blocks that would stop exonucleases in addition to Xrn1. The ability of an xrRNA to block RNase J1, a 5'→3' exonuclease from bacteria with no known structural homology to Xrn1, was tested. The xrRNA was able to block bacterial RNase J1 and other enzymes (see FIG. 12) suggesting that the technology developed and described herein could be broadly applied.

Chemical Modification of the RNA

Figure 11:
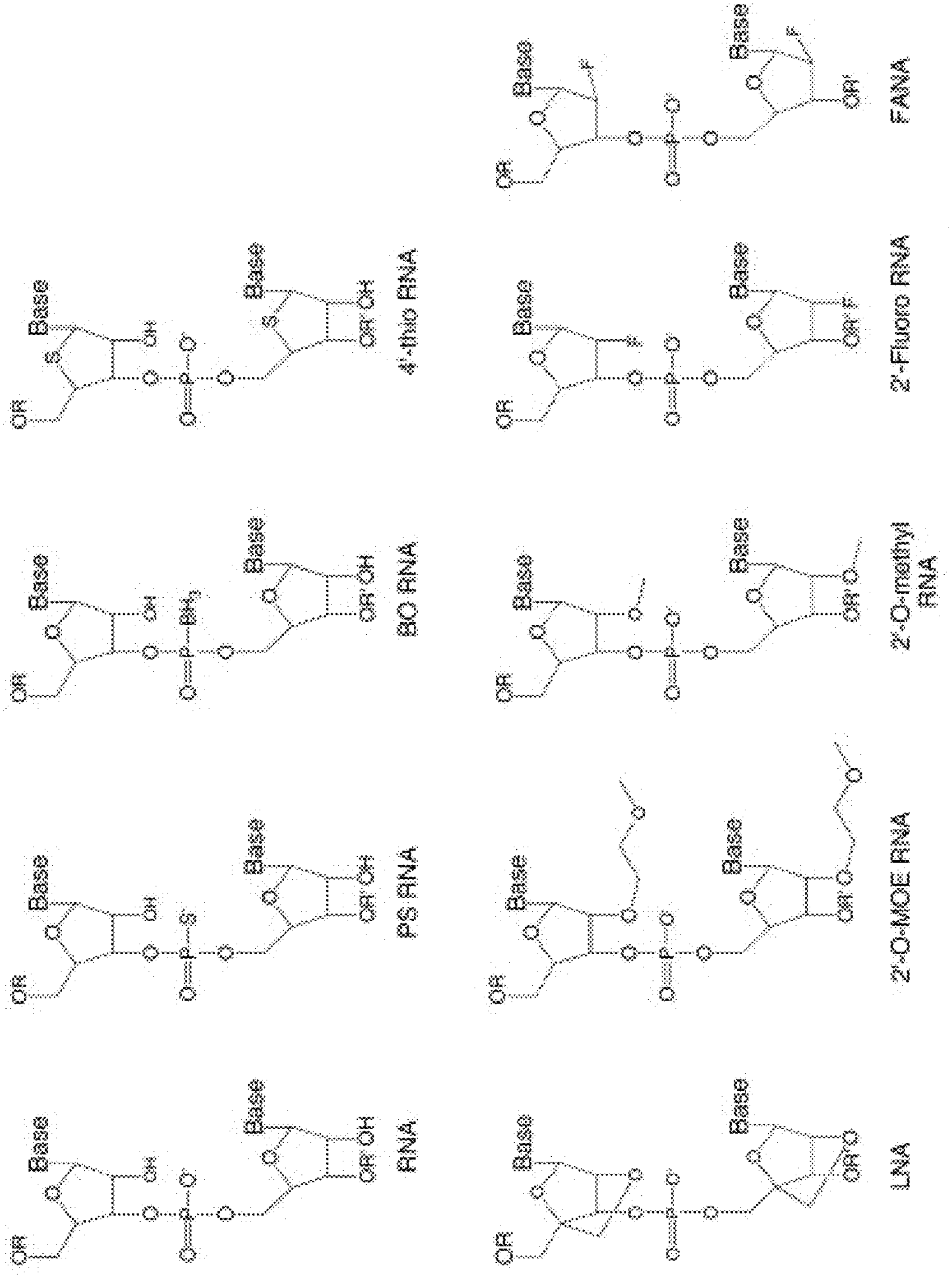
FIG. 11 depicts some types of chemical modification of the RNA that be included in the current invention. For example, the chemical modification may comprise inclusion of phosphorothioate linkages, boranophosphate linkages, locked nucleic acid, 2'-modifications, 4'-thio modified RNA, ribo-difluorotoluyl nucleotide, and uncharged nucleic acid mimics, as described by Corey (2007) J. Clin. Invest. 117(12), 3615-3622 [14], herein encorporated by reference.
Figure 11:
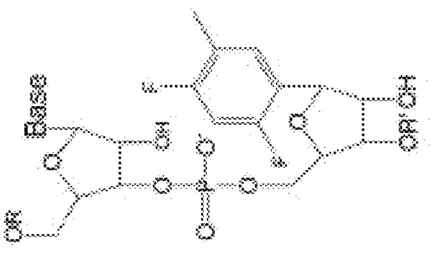
Figure 11:
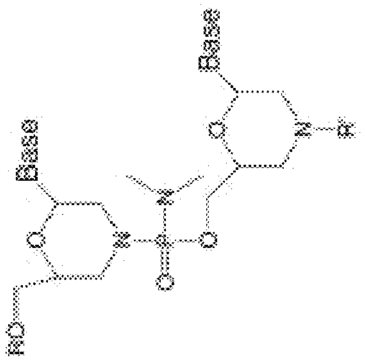
Figure 11:
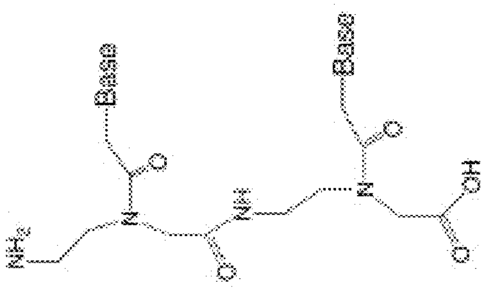

There are many methods of chemical modification of RNA known in the art. In some embodiments, the chemical modification may comprise chemical modification of one xrRNA containing RNA sequence. In one embodiment, wherein there is a substrate strand and a protecting strand, one or both strands may be chemically modified. Although not limiting the current invention to any particular means or type of chemical modification, in one embodiment, chemical modification comprises modification of the 3' or 5' ends of said RNA strands. In one embodiment, the 5' modification may include: addition of 7-methylguanosine (m7G) and other synthetic additions. In one embodiment, the 3' modification may include: addition of a poly(A) tail and other synthetic additions In some embodiments, chemical modification of RNA may also comprise inclusion of phosphorothioate linkages, boranophosphate linkages, locked nucleic acid, 2'-modifications, 4'-thio modified RNA, ribo-difluorotoluyl nucleotide, and uncharged nucleic acid mimics, as described by Corey 2007 J. Clin. Invest. 117(12), 3615-3622 [14], herein encorporated by reference. See FIG. 11. Replacing one nonbridging oxygen atom on the backbone phosphate between two ribonucleotides with a sulphur atom creates a phosphorothioate (PS) linkage. In one embodiment, the current invention contemplates modifying the phosphate backbone of an oligonucleotide is the introduction of a boron atom in place of one of the nonbridging oxygen atoms to create a boron-phosphorous linkage. In one embodiment, the current invention contemplates the use of locked nucleic acid (LNA) nucleotides that contain a methylene bridge between the 2' and 4' carbons of the ribose ring. In one embodiment, the current invention contemplates the use of substitutions for the hydroxyl group on the 2' carbon atom of the ribose ring of particular nucleotides. In one embodiment, the current invention contemplates the use of 4'-Thio modified nucleotides, which contain a sulphur atom in place of oxygen attached to the 4' carbon of the ribose ring. In one embodiment, the current invention contemplates introduction of ribo-difluorotoluyl (rF) nucleotides (65). In one embodiment, single-stranded uncharged nucleic acid mimics, such as peptide nucleic acids (PNAs) (66, 67) and morpholino oligomers (68) may be useful as partial or full replacements for nucleotides in the RNA.

Thus, specific compositions and methods of protecting RNAs from degradation using engineered viral RNAs have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Anderson, M. L. M. and Young, B. D. (1985) "Quantitative Filter Hybridization," in *Nucleic Acid Hybridisation: A Practical Approach* (Hames, B. D. and Higgins, S. J., Eds.), pp 73-111, Oxford University Press, USA.
2. Dieffenbach, C. W. and Dveksler, G. S. (1995) *PCR Primer, a Laboratory Manual*, Cold Spring Harbor Laboratory Press, Plainview, N.Y
3. Mullis, K. B. et al. "Process for Amplifying, Detecting, and/or -Cloning Nucleic Acid Sequences," U.S. Pat. No. 4,683,195, application Ser. No. 06/828,144, filed Feb. 7, 1986. (issued Jul. 28, 1987).
4. Mullis, K. B. "Process for Amplifying Nucleic Acid Sequences," U.S. Pat. No. 4,683,202, application Ser. No. 06/791,308, filed Oct. 25, 1985. (issued Jul. 28, 1987).
5. Maniatis, T. et al. (1987) "Regulation of Inducible and Tissue-Specific Gene Expression," *Science* 236(4806), 1237-1245.
6. Sambrook, J. et al., (Eds.) (1989) *Molecular Cloning: A Laboratory Manual*, 2nd ed., Cold Spring Harbor Laboratory Press, New York.
7. Rubenstein, K. E. and Ullman, E. F. "Enzyme Amplification Assay," U.S. Pat. No. 3,817,837, Application 304, 156, filed Nov. 6, 1972. (issued Jun. 18, 1974).
8. Schuurs, A. H. W. M. and Van Weemen, B. K. "Process for the Demonstration and Determination of Low Molecular Compounds and of Proteins Capable of Binding These Compounds Specifically," U.S. Pat. No. 3,850,752, application Ser. No. 05/193,702, filed Oct. 29, 1971. (issued Nov. 29, 1974).
9. Kronick, M. N. and Little, W. A. "Fluorescent Immunoassay Employing Total Reflection for Activation," U.S. Pat. No. 3,939,350, application Ser. No. 05/465,009, filed Apr. 29, 1974. (issued Feb. 17, 1976).
10. Ullman, E. F. and Schwarzberg, M. "Fluorescence Quenching with Immunological Pairs in Immunoassays," U.S. Pat. No. 3,996,345, application Ser. No. 05/591,386, filed Jun. 30, 1976. (issued Dec. 7, 1976).
11. Maggio, E. T. "Kit for Carrying out Chemically Induced Fluorescence Immunoassay," U.S. Pat. No. 4,277,437, application Ser. No. 06/101,935, filed Dec. 10, 1979. (issued Jul. 7, 1981).
12. Litman, D. J. et al. "Macromolecular Environment Control in Specific Receptor Assays," U.S. Pat. No. 4,275,149, application Ser. No. 05/964,099, filed Nov. 24, 1978. (issued Jun. 23, 1981).
13. Tom, H. K. and Rowley, G. L. "Concentrating Zone Method in Heterogeneous Immunoassays," U.S. Pat. No. 4,366,241, application Ser. No. 06/176,177, filed Aug. 7, 1980. (issued Dec. 28, 1982).
14. Corey, D. R. (2007) "Chemical Modification: The Key to Clinical Application of RNA Interference?," *J. Clin. Invest.* 117(12), 3615-3622.
15. Chapman, E. G. et al. (2014) "The Structural Basis of Pathogenic Subgenomic Flavivirus RNA (sfRNA) Production," *Science* 344(6181), 307-310.
16. Han, S.-P. et al. "Signal Activated RNA Interference," U.S. Pat. No. 9,029,524, application Ser. No. 12/316,372, filed Dec. 10, 2008. (issued May 12, 2015).
17. Chapman, E. G. et al. (2014) "RNA Structures That Resist Degradation by Xrn1 Produce a Pathogenic Dengue Virus RNA," *eLife* 3, e01892.
18. Kieft, J. S. et al. (2015) "New Hypotheses Derived from the Structure of a Flaviviral Xrn1-Resistant RNA: Conservation, Folding, and Host Adaptation," *RNA Biol.*
19. Moon, S. L. et al. (2012) "A Noncoding RNA Produced by Arthropod-Borne Flaviviruses Inhibits the Cellular Exoribonuclease XRN1 and Alters Host mRNA Stability," *RNA* 18(11), 2029-2040.

20. Burke, D. H. et al. (1996) "Bent Pseudoknots and Novel RNA Inhibitors of Type 1 Human Immunodeficiency Virus (HIV-1) Reverse Transcriptase," *J. Mol. Biol.* 264 (4), 650-666.
21. Froehler, B. C. "Exonuclease-Resistant Oligonucleotides," U.S. Pat. No. 5,256,775, application Ser. No. 07/555,522, filed Jun. 5, 1990. (issued Oct. 26, 1993).
22. Han, S.-P. et al. "Exonuclease Resistant Polynucleotide and Related Duplex Polynucleotides, Constructs, Compositions, Methods and Systems," United States Patent Application Publication Number US 2014-0329880 A1, application Ser. No. 14/093,387, filed Nov. 29, 2013. (published Nov. 6, 2014).
23. Lin, K.-C. et al. (2004) "Accumulation of a 3'-Terminal Genome Fragment in Japanese Encephalitis Virus-Infected Mammalian and Mosquito Cells," *J Virol.* 78(10), 5133-5138.
29. Jones, C. I. et al. (2012) "The 5'-→3' Exoribonuclease XRN1/Pacman and Its Functions in Cellular Processes and Development," *Wiley Interdiscip. Rev. RNA* 3(4), 455-468.
30. Wang, Z. et al. (2011) "The Cap-Binding Translation Initiation Factor, Eif4e, Binds a Pseudoknot in a Viral Cap-Independent Translation Element," *Structure* 19(6), 868-880.
31. Batey, R. T. (2012) "Structure and Mechanism of Purine Binding Riboswitches," *Q. Rev. Biophys* 45(3), 345-381.
32. Paige, J. S. et al. (2011) "RNA Mimics of Green Fluorescent Protein," *Science* 333(6042), 642-646.
33. Jaffrey, S. (2014) "Imaging RNA and RNA Biology Using RNA Mimics of Green Fluorescent Protein (347.1)," *FASEB J.* 28 (1 Supplement).

SEQUENCE LISTING

```
<160> NUMBER OF SEQ ID NOS: 2

<210> SEQ ID NO 1
<211> LENGTH: 78
<212> TYPE: DNA
<213> ORGANISM: Artificial
<220> FEATURE:
<223> OTHER INFORMATION: Synthetic heterologous RNA sequence

<400> SEQUENCE: 1

gggccggcaa aacuaacaug aaaacaaggc uaaaagucag gucggauuac ccuuuuggau     60

cccgacuggc gagagcca                                                    78


<210> SEQ ID NO 2
<211> LENGTH: 60
<212> TYPE: DNA
<213> ORGANISM: Artificial
<220> FEATURE:
<223> OTHER INFORMATION: Synthetic exonuclease resistance-providing RNA
      sequence

<400> SEQUENCE: 2

ggguaauccg ccauaguacg gaaaaaacua ugcuaccugu gagccccguc caaggacguu     60
```

24. Urosevic, N. et al. (1997) "Molecular Characterization of Virus-Specific RNA Produced in the Brains of Flavivirus-Susceptible and -Resistant Mice after Challenge with Murray Valley Encephalitis Virus," *J Gen. Virol.* 78(1), 23-29.
25. Scherbik, S. V. et al. (2006) "RNase L Plays a Role in the Antiviral Response to West Nile Virus," *J. Virol.* 80(6), 2987-2999.
26. Funk, A. et al. (2010) "RNA Structures Required for Production of Subgenomic Flavivirus RNA," *J Virol.* 84(21), 11407-11417.
27. Pijlman, G. P. et al. (2008) "A Highly Structured, Nuclease-Resistant, Noncoding RNA Produced by Flaviviruses Is Required for Pathogenicity," *Cell Host Microbe* 4(6), 579-591.
28. Silva, P. A. G. C. et al. (2010) "An RNA Pseudoknot Is Required for Production of Yellow Fever Virus Subgenomic RNA by the Host Nuclease XRN1," *J. Virol.* 84(21), 11395-11406.

We claim:

1. A ribonucleic acid (RNA) duplex comprising a synthetic first RNA sequence that provides exonuclease resistance to the RNA duplex when hybridized to a heterologous second RNA sequence without exonuclease resistance, wherein a region of said synthetic RNA sequence and a region of said heterologous RNA sequence hybridize to form an interwoven pseudoknot structure, wherein the synthetic first RNA sequence that provides exonuclease resistance to the RNA duplex comprises a sequence of nucleotides 10-60 of SEQ ID NO:2.

2. The RNA duplex of claim 1, wherein the interwoven pseudoknot structure comprises a conserved three-way junction.

3. The RNA duplex of claim 1, wherein the heterologous second RNA sequence comprises a naturally occurring RNA sequence.

4. The RNA duplex of claim 1, wherein the synthetic first RNA sequence further comprises a further heterologous RNA sequence ligated to the 3' end of the synthetic RNA sequence.

5. The RNA duplex of claim 4, wherein the further heterologous RNA sequence ligated to the 3' end of the synthetic first RNA sequence comprises a small molecule sensing riboswitch.

6. The RNA duplex of claim 4, wherein the synthetic first RNA sequence further comprises a translation initiation element.

7. The RNA duplex of claim 5, wherein the small molecule sensing riboswitch disrupts the interwoven pseudoknot structure in a presence of a small molecule sensed by the small molecule sensing riboswitch.

8. The RNA duplex of claim 4, wherein the heterologous second RNA sequence comprises an open reading frame.

9. The RNA duplex of claim 4, wherein the heterologous second RNA sequence comprises a protein binding sequence.

10. The RNA duplex of claim 4, wherein the heterologous second RNA sequence comprises a spinach sequence.

11. The RNA duplex of claim 1, wherein the RNA duplex comprises a chemical modification of either the 5' end or the 3' end of the synthetic first RNA sequence, and/or the heterologous second RNA sequence, in the RNA duplex.

12. The RNA duplex of claim 1, wherein the RNA duplex comprises at least one chemically modified nucleotide.

13. The RNA duplex of claim 1, wherein the synthetic first RNA sequence comprises a sequence of GGGUAAUCCGCCAUAGUACGGAAAAAACUAU GCUACCUGUGAGCCCCGUCCAAGGACGUU (SEQ ID NO:2).

14. The RNA duplex of claim 1, wherein the heterologous second RNA sequence comprises a sequence of nucleotides 1-43 of SEQ ID NO:1.

15. A ribonucleic acid (RNA) duplex comprising two ribonucleic acids (RNAs):

a synthetic first RNA; and a heterologous second RNA, wherein the synthetic first RNA provides exonuclease resistance to the RNA duplex when hybridized to a heterologous second RNA, wherein a region of said synthetic first RNA and a region of said heterologous second RNA hybridize to form an interwoven pseudoknot structure comprising a conserved three-way junction, and wherein the interwoven pseudoknot structure of the RNA duplex comprises sequences that form P3/L3 stem loop and P4/L4 stem loop structures of a flavivirus (FV) xrRNA1 or xrRNA2 element.

16. The RNA duplex of claim 15, wherein the sequences that form the P3/L3 stem loop and P4/L4 stem loop structures comprise P3/L3 stem loop, P1, S4, and P4/L4 stem loop sequences found downstream of P2/L2 stem loop sequences of a FV xrRNA1 or xrRNA2 element.

17. The RNA duplex of claim 16, wherein the P3/L3 stem loop, P1, S4, and P4/L4 stem loop sequences found downstream of the P2/L2 stem loop sequences of the FV xrRNA1 or xrRNA2 element comprise a GCCA sequence at a 5' end of the P3/L3 stem loop, P1, S4, and P4/L4 stem loop sequences.

18. The RNA duplex of claim 15, wherein the FV xrRNA1 or xrRNA2 element is from a flavivirus selected from the group consisting of Dengue (DENV), Yellow Fever (YFV), Japanese Encephalitis (JEV), West Nile (WNV), Murray Valley Encephalitis (MVE), and Zika virus.

19. The RNA duplex of claim 15, wherein the FV xrRNA1 or xrRNA2 element is from a DENV xrRNA1 or xrRNA2 element.

20. The RNA duplex of claim 15, wherein the synthetic first RNA that provides exonuclease resistance to the RNA duplex comprises a sequence of nucleotides 10-60 of SEQ ID NO:2.

* * * * *